United States Patent
May et al.

(10) Patent No.: US 9,353,109 B2
(45) Date of Patent: May 31, 2016

(54) FLINDERSIA ALKALOIDS, DERIVATIVES AND ANALOGS: COMPOSITIONS AND METHODS FOR PRODUCING THE SAME

(71) Applicants: Jeremy A. May, Pearland, TX (US); Ravikrishna Vallakati, Houston, TX (US)

(72) Inventors: Jeremy A. May, Pearland, TX (US); Ravikrishna Vallakati, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 14/753,480

(22) Filed: Jun. 29, 2015

(65) Prior Publication Data

US 2015/0299196 A1    Oct. 22, 2015

Related U.S. Application Data

(62) Division of application No. 13/744,884, filed on Jan. 18, 2013, now Pat. No. 9,067,946.

(60) Provisional application No. 61/588,378, filed on Jan. 19, 2012.

(51) Int. Cl.
| | |
|---|---|
| *C07D 487/06* | (2006.01) |
| *C07D 471/02* | (2006.01) |
| *C07D 471/04* | (2006.01) |
| *C07D 487/04* | (2006.01) |
| *C07D 487/08* | (2006.01) |
| *C07D 471/06* | (2006.01) |
| *C07D 471/16* | (2006.01) |

(52) U.S. Cl.
CPC ............ *C07D 471/04* (2013.01); *C07D 471/06* (2013.01); *C07D 471/16* (2013.01); *C07D 487/04* (2013.01); *C07D 487/06* (2013.01); *C07D 487/08* (2013.01)

(58) Field of Classification Search
USPC ..................................... 548/420, 428; 546/85
See application file for complete search history.

(56) References Cited

U.S. PATENT DOCUMENTS 9,067,946 B2 * 6/2015 May ...................... C07D 87/06

OTHER PUBLICATIONS

Tillequin, F. et al.: Biomimetic synthesis of Borreverine and isoborreverine. J. C. S. Chem. Comm., pp. 826-828, 1978.*
Yamanaka, E. et al.: A development of pictet-spengler reaction in aprotic media using chloroformates; a short synthesis of Borrerine. Heterocycles, vol. 22, pp. 371-374, 1984.*

* cited by examiner

*Primary Examiner* — Charanjit Aulakh
(74) *Attorney, Agent, or Firm* — Benjamin Aaron Adler

(57) ABSTRACT

The present invention provides methods for chemically synthesizing analogs and derivatives of naturally-occurring *Flindersia* alkaloids. Generally, the precursor borrerine is synthesized from tryptamine in the presence of an alkylating agent, an acylating agent and a reducing agent and dimerized in the presence of an acid, for example, trifluoroacetic acid, hydrochloric acid or acetic acid to yield the products. Analog and derivative compounds are produced by derivatizing one or more of the tryptamine, alkylating agent or acylating agent. Also provided are the synthetic alkaloids and derivatives and analogs thereof produced by the synthetic methods.

9 Claims, 8 Drawing Sheets

FLINDERSIA ALKALOIDS, DERIVATIVES AND ANALOGS: COMPOSITIONS AND METHODS FOR PRODUCING THE SAME

CROSS-REFERENCE TO RELATED APPLICATION

This application is a divisional under 37 C.F.R. §120 of pending non-provisional application U.S. Ser. No. 13/744,884, filed Jan. 18, 2013, which claims benefit of priority under 35 U.S.C. §119(e) of provisional application U.S. Ser. No. 61/588,378, filed Jan. 19, 2012, the entirety of both of which are hereby incorporated by reference.

BACKGROUND OF THE INVENTION

1. Field of the Invention

The present invention relates generally to the fields of organic chemical synthesis and medicinal organic plant compounds. More specifically, the present invention relates to methods for the large-scale synthesis of naturally occurring medicinal organic compounds.

2. Description of the Related Art

Malaria is the leading cause of child mortality worldwide. However, the mosquito-borne disease has been classified as an "orphan disease" because the poverty of the afflicted regions does not sustain for-profit drug discovery. The rapid evolution of drug-resistant strains of the disease magnifies the tragedy by rendering cheaper treatments ineffective. Other than mosquito eradication strategies, historically the most effective approaches to curbing malaria have been small molecule-based treatments derived from natural products, for example, plants.

Avery et al. investigated the activity of *Flindersia* alkaloids (1-3) which demonstrate toxicity against *Plasmodium falciparum*, the malarial strain responsible for most deaths. Several of the compounds, for example, flinderoles A, B and C, isoborreverine, dimethylisoborreverine, chloroquine and artemisinin show effectiveness toward chloroquine-resistant *falciparum* strains at concentrations that do not affect mammalian cells' viability. The Avery group determined that while the *Flindersia* alkaloids target the hemoglobin metabolism of *P. falciparum*, they do not mimic the heme-binding action of the quinoline alkaloids. It is possible that they could act nonspecifically either by inhibiting a known protein for hemoglobin metabolism, e.g., a hemoglobin protease or a histidine-rich protein that sequesters toxic heme as hemozoin, or by inhibiting an as-yet-undisclosed target, however, the mechanism of these compounds remains unknown. Consequently, further research on the development of new antimalarial therapeutics is needed.

There is a recognized need for improved methods of biomimetic synthesis of naturally occurring organic compounds to gain access to these compounds for biological testing and development of therapeutic compounds based on the same. The prior art is deficient in the lack of a large-scale biomimetic synthesis of organic plant compounds via a method requiring few steps. The present invention fulfills this longstanding need and desire in the art.

SUMMARY OF THE INVENTION

The present invention is directed to a method for chemically synthesizing a naturally occurring alkaloid compound. The method comprises synthesizing a precursor of the alkaloid compound. Subsequently, the synthesized precursor is dimerized in the presence of an acid to yield the synthetic alkaloid compound.

The present invention is further directed to a related method where the precursor is borrerine and the synthesizing step comprises the steps of adding an alkylating agent to tryptamine or to a derivative thereof, adding an acylating agent in the presence of a base to form an α-substituted piperidinyl-N-carbamate intermediate thereof; and adding a strong reducing agent to the intermediate to produce borrerine. The present invention is further directed to another related method where the dimerizing step further comprises methylating the synthesized precursor prior to addition of the acid.

The present invention also is further directed to a chemical synthetic method for producing a naturally-occurring *Flindersia* alkaloid. The method comprises the steps of synthesizing borrerine from tryptamine and dimerizing the synthesized borrerine in the presence of an acid to yield the synthetic alkaloid compound. The method comprises synthesizing a precursor of the alkaloid compound. Subsequently, the synthesized precursor is dimerized in the presence of an acid to yield the synthetic alkaloid compound.

The present invention is directed further to a chemical synthetic method for producing an analog compound of a naturally-occurring *Flindersia* alkaloid. The method comprises synthesizing a derivative of borrerine from a tryptamine derivative. Subsequently, the synthesized borrerine derivative is dimerized in the presence of an acid to yield the synthetic analog compound.

The present invention is directed further still to the synthetic alkaloids, derivatives thereof and analogs thereof produced by the chemical synthetic methods described herein.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
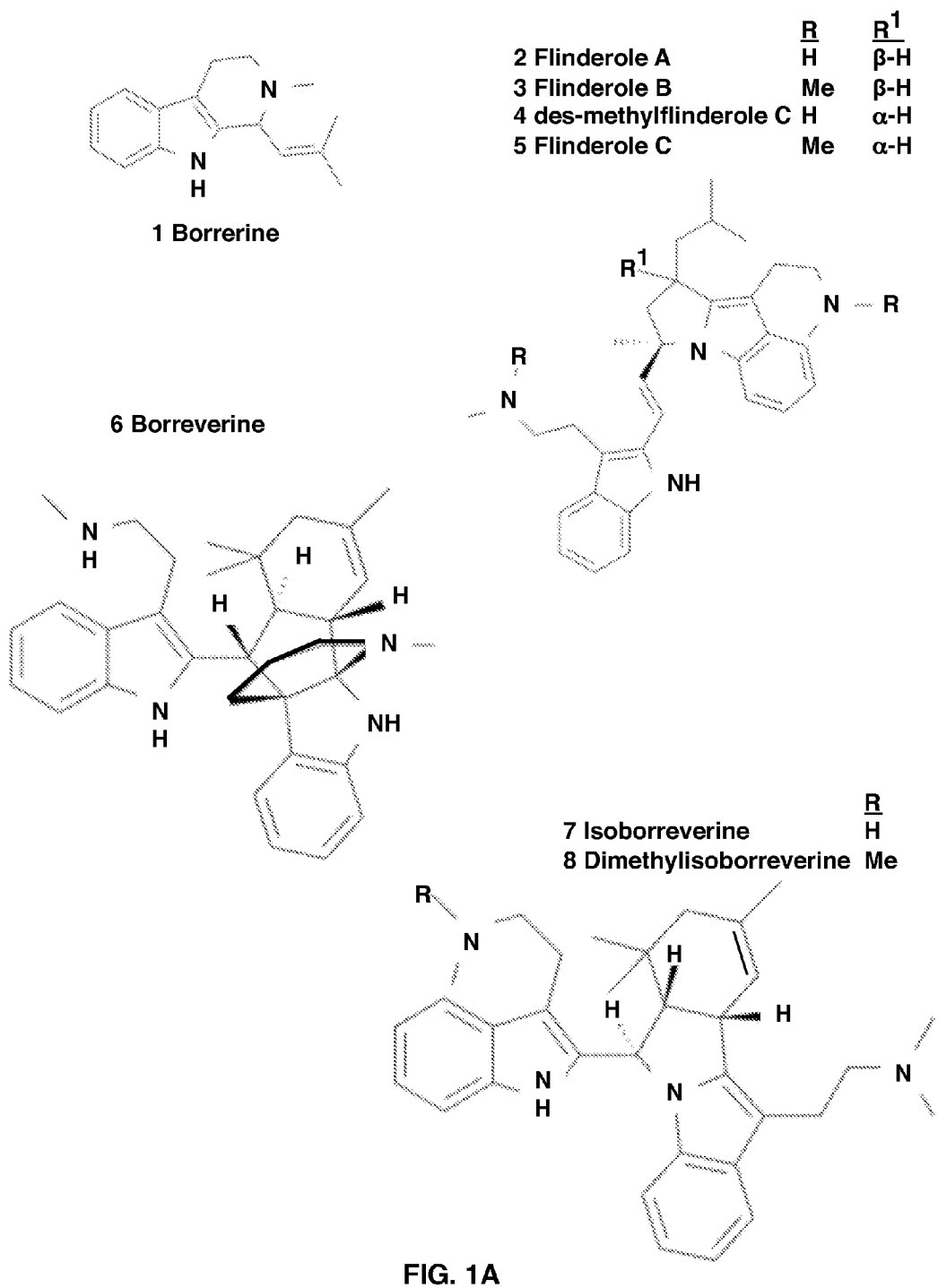
FIG. 1A depicts the chemical structures of *Flindersia* alkaloids. All but 1 and 6 are known to have selective antimalarial activities.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "analog" refers to chemical compounds that have similar structures and similar chemical properties to those of another compound, but differs from it by a single element or group.

As used herein, the term "derivative" refers to a substance or compound obtained from, or regarded as derived from, another substance or compound.

In one embodiment of the present invention, there is provided a method for chemically synthesizing a naturally occurring alkaloid compound, comprising the steps of synthesizing a precursor of the alkaloid compound; dimerizing the synthesized precursor in the presence of an acid to yield the synthetic alkaloid compound.

In an aspect of this embodiment, the precursor is borrerine and the synthesizing step comprises adding an alkylating agent to tryptamine or to a derivative thereof; adding an acylating agent in the presence of a base to form a substituted piperidinyl-N-carbamate intermediate; and adding a strong reducing agent to the intermediate to produce borrerine. A representative example of the alkylating agent is 3-methyl 2-butenal, a representative example of the acylating agent is methyl chloroformate, a representative example of the strong reducing agent is lithium aluminum hydride and the base is pyridine. In this aspect, the tryptamine may be derivatized independently at one or more of C4, C5, C6, and C7 with hydroxy, methoxy, acetoxy, benzyloxy, sulfomethyl, amino, acetate, methyl, ethyl, iso-propyl, t-butyl, trifluoromethyl, cyano, methylformate, nitrate, or halide. Furthermore, a representative example of the alkylating agent is an α-β-unsaturated aldehyde. Representative examples are, including but not limited to, 2,3-dimethyl-3-phenyl-2-propenal, 2,3-dimethyl-3-isopropyl-2-propenal, 2,3-dimethyl-3-thiazolyl-2-propenal, 2,3-dimethyl-3-imidazolyl-2-propenal, 3-phenyl-2-propenal, 3-isopropyl-2-propenal, 3-thiazolyl-2-propenal, 3-imidazolyl-2-propenal, benzylformaldehyde, 3-methyl-2-propynal, or a bis-aldehyde. In addition, a representative example of the acylating agent is a chloroformaldehyde substituted with t-butyl, octanyl, phenyl, trifluoromethyl, 2-methylthiazole, 2-methylimidazole, or 1,2-dimethoxyethane.

In a related aspect, the synthesized precursor is borrerine, the acid is trifluoroacetic acid and the synthetic alkaloid is isoborreverine or borreverine. In alternative aspects, the acid is hydrochloric acid or acetic acid and the synthetic alkaloid is flinderole A and des-methylflinderole C.

Further to this embodiment, the dimerizing step comprises methylating the synthesized precursor with a methylating agent prior to addition of the acid. Particularly, the methylating agent is methyl triflate or dimethyl sulfate, the acid is trifluoroacetic acid or acetic acid and the synthetic alkaloid compound is flinderole B, flinderole C, or dimethylisoborreverine.

In a related embodiment of the present invention there is provided a synthetic alkaloid compound produced by the method as described supra.

In another embodiment of the present invention there is provided a chemical synthetic method for producing a naturally-occurring *Flindersia* alkaloid, comprising the steps of synthesizing borrerine from tryptamine; and dimerizing the synthesized borrerine in the presence of an acid to yield the synthetic alkaloid compound.

In this embodiment, the synthesizing step may comprise adding 3-methyl 2-butenal to tryptamine; adding methyl chloroformate in the presence of a base to form an α-substituted piperidinyl-N-carbamate intermediate; and adding a strong reducing agent to the intermediate to produce borrerine. Particularly, a representative example of the reducing agent is lithium aluminum hydride and of the base is pyridine. Also, a representative example of the acid is trifluoroacetic acid, hydrochloric acid or acetic acid and a representative example of the synthetic alkaloid compound is flinderole A, des-methylflinderole C, isoborreverine, or borreverine.

Further to this embodiment the dimerizing step comprises methylating the synthesized precursor with a methylating agent prior to addition of the acid. Particularly, the methylating agent is methyl triflate or dimethyl sulfate, the acid is trifluoroacetic acid or acetic acid, and the synthetic alkaloid compound is flinderole B, flinderole C, or dimethylisoborreverine.

In a related embodiment of the present invention there is provided a synthetic *Flindersia* alkaloid produced by the method as described supra.

In yet another embodiment of the present invention, there is provided a chemical synthetic method for producing an analog compound of a naturally-occurring *Flindersia* alkaloid, comprising the steps of synthesizing a derivative of borrerine from a tryptamine derivative; and dimerizing the synthesized borrerine derivative in the presence of an acid to yield the synthetic analog compound.

In this embodiment, the tryptamine derivative, the derivative of 3-methyl-2-butenal and the aldehyde derivative of methyl chloroformate, the reducing agent, the base, and the acid are as described supra. Also in this embodiment the borrerine derivative comprises one or more substituents from the tryptamine derivative on the phenyl ring or α-substituents from the 3-methyl-2-butenal derivative or N-substituents on the piperidinyl ring.

In a related embodiment of the present invention there is provided a synthetic *Flindersia* alkaloid analog compound produced by the method as described supra.

Provided herein are novel, efficient synthetic methods for making large quantities of naturally occurring organic compounds, for example, antimalarial therapeutics that are similar in structure to those extracted from natural sources such as *Flindersia* plants, as well as methods for generating new structural analogs and functional derivatives of those natural products and for creating a library of compounds with specific anti-plasmodial activity.

Particularly, a large scale synthesis of antimalarial natural products requires only three synthetic steps, thereby reducing the steps in the synthetic route by over 80% compared to known synthetic methods which require 14 steps using the method of Dethe et al. (5) or 18 steps by the method of Toste et al. (6). The disclosed methods are also well suited for making related compounds that are likely to also possess antimalarial properties or other anti-microbial activities. The significant reduction in the number of steps required for the preparation of such compounds has significant positive implications for the treatment and prevention of malaria in that it allows for a more efficient and cheaper manufacturing process, therefore lowering the cost to access for populations in need of such treatment. At the time of the invention provided herein, no better alternatives exist.

Generally, the synthetic mechanism for making isoborreverine, dimethylisoborreverine, flinderoles, or derivatives or analogs thereof, as described in Examples 1 and 2, first requires the synthesis of the *Flindersia* alkaloid precursor borrerine. In the first steps, borrerine is synthesized from tryptamine via an intermediate pyridinyl carbamate which is subsequently reduced to the product. In the final step acid promoted dimerization of borrerine produces flinderole A, des-methylflinerole C, isoborreverine, and borreverine. Alternatively, the final step is a direct methylation of borrerine followed by treatment with an acid to produce flinderole B, flinderole C and dimethyl isoborreverine.

Figure 2:
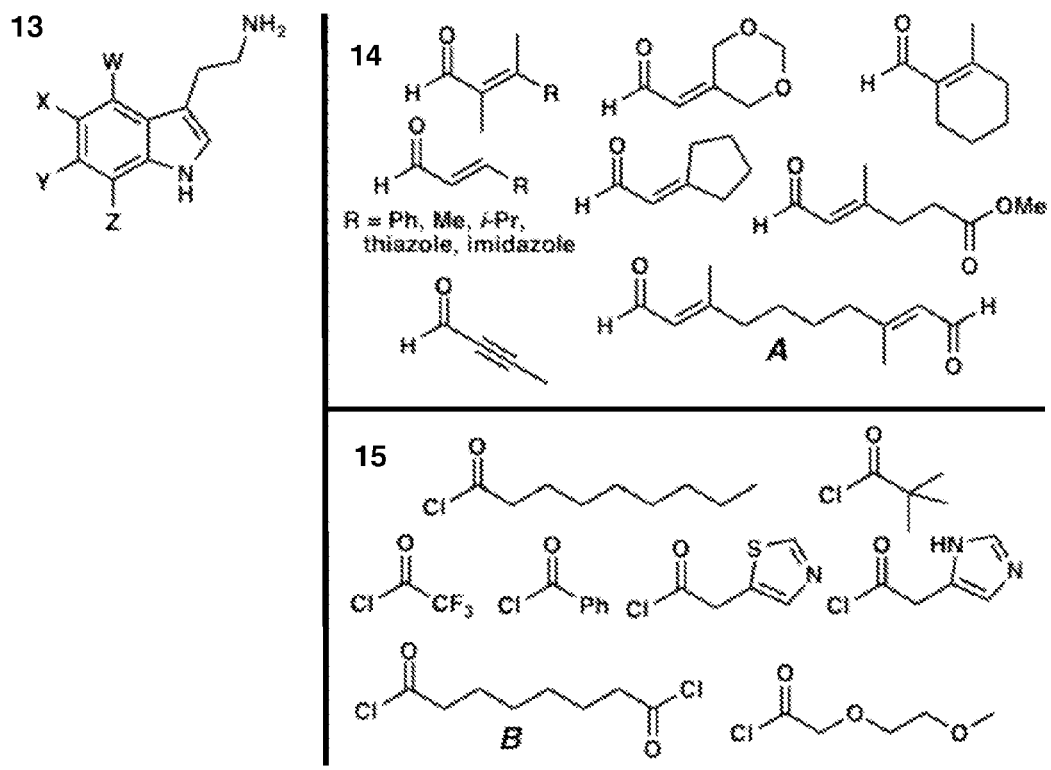
FIG. 2 are examples of alternate synthetic compounds for library synthesis. Modifications for tryptamine 13, aldehyde 14 and acylating group 15, including the incorporation of an electrophile for nitrogen addition, are depicted.

Moreover, the disclosed chemical synthetic methods are also well adapted for making structural analogues of the synthesized *Flindersia* alkaloids these steps are utilized for the chemical synthesis of derivatives and analog compounds with antimalarial activity by synthesizing a borrerine derivative or analog via a derivatized tryptamine and/or derivatized reagents used in the production of borrerine (see FIG. 2). Such synthetic derivative and analog alkaloids can be optimized for their potency and selectivity for malaria, Chagas' disease, and other protozoan-caused infectious diseases, while minimizing undesirable side effects as per the flinderoles and isoborreverines described herein.

The synthetic derivative and analog alkaloids can comprise a compound library with which to determine structure-activity relationships of these novel malaria therapeutics. The short biomimetic synthetic methods described herein provide efficient access to each natural *Flindersia* alkaloid. Moreover, the compound library may be expanded and diversified by further incorporating compounds useful in molecular biological techniques, such as luminescent or fluorescent dyes, alkylating agent, crosslinking agents. In addition, 2- and 3-substituted indoles may be used in place of tryptamine to further broaden the library. The library may include only the skeletons of the compounds to aid in determining atomic groups or pharmacophores essential for therapeutic activity.

The following examples are given for the purpose of illustrating various embodiments of the invention and are not meant to limit the present invention in any fashion.

Example 1

Effects of Acids on Dimerization of Borrerine 1

The synthetic borrerine 1 was treated with 2 equivalents of TFA in benzene at 65° C. for 40 minutes (Table 1, entry 2). Borrerine was consumed as observed by TLC analysis, and two new closely spaced product spots appeared. $^1$H NMR analysis of the crude mixture showed evidence of isoborreverine as one of the major products. The remaining $^1$H NMR peaks corresponded to the spectra of flinderole A and desmethylflinderole C. In fact, the flinderole diastereomers appeared to be produced in roughly the same amount as isoborreverine. Contrary to previous reports, only trace amounts of borreverine were observed. While isoborreverine was readily isolated via flash chromatography, the separation of the flinderoles required the use of reverse-phase HPLC. This purification allowed the alkaloid identities and the ratios of their formation as observed in the $^1$H NMR spectra of the crude mixtures to be confirmed.

In an effort to reproduce the original report of borreverine 6 formation a range of TFA equivalents, reaction times, and reaction temperatures were screened (entries 1-7). $^1$H NMR peaks associated with borreverine were occasionally observed, but integration indicated that it was produced in only trace amounts. In retrospect, this is unsurprising, as the stereochemistry of borreverine would have to arise from a less-favorable exo-Diels-Alder reaction in the initial step (Scheme 1). This observation may have relevance to the alkaloids biosynthesis, as Avery et al. did not observe any borreverine in the *Flindersia* species that produced the flinderoles (3). Changing the solvent to chloroform gave the flinderoles as a majority of the crude mixture (entry 8). The use of THF, dioxane, and DMF as solvents resulted in no reaction. Interestingly, the omission of solvent resulted in exclusive formation of isoborreverine. Table 1 shows the results of the treatment of borrerine with TFA and Table 2 shows the results of the effects of various acids on dimerization. In both Tables 1 and 2 the ratio of product yields were determined by integration of $^1$H NMR peaks and the combined yields were all above 95% with the balance as borrerine 1 for entries identified as c. In Table 2 for entry 10 6 equivalents of acid were utilized and for entry 11 150 equivalents of acid were utilized.

TABLE 1

| | | | |
|---|---|---|---|
| | | Flinderole A | 2 |
| | TFA | Desmethylflinderole C | 4 |
| | conditions | Isoborreverine | 7 |
| | | Borreverine | 6 |

1 Borrerine

| | TFA | | | | ratio of product yields$^{a,t}$ | | | |
|---|---|---|---|---|---|---|---|---|
| entry | TFA equiv | solvent | temp | time | 2: | 4: | 7: | 6 |
| 1 | 1.0 | benzene | 65° C. | 2 h | 0 | 0 | 0 | 0$^c$ |
| 2 | 2.0 | benzene | 25° C. | 40 min | 41 | 30 | 28 | 1 |
| 3 | 2.0 | benzene | 55° C. | 82 min | 38 | 33 | 29 | 0 |

TABLE 1-continued

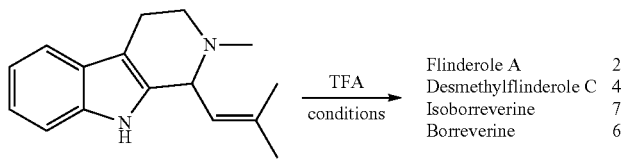

1 Borrerine

Flinderole A 2
Desmethylflinderole C 4
Isoborreverine 7
Borreverine 6

| entry | TFA equiv | solvent | temp | time | ratio of product yields[a,t] 2: | 4: | 7: | 6 |
|---|---|---|---|---|---|---|---|---|
| 4 | 3.0 | benzene | 40° C. | 2 h | 34 | 32 | 34 | 0 |
| 5 | 3.0 | benzene | 65° C. | 30 min | 28 | 28 | 43 | 1 |
| 6 | 6.0 | benzene | 0-20° C. | 24 min | 16 | 13 | 34 | 0[c] |
| 7 | 6.0 | benzene | 40° C. | 30 min | 17 | 17 | 21 | 0[c] |
| 8 | 2.0 | CHCl$_3$ | 45° C. | 30 min | 28 | 28 | 7 | 1[c] |
| 9 | 2.0 | none | 65° C. | 48 h | 0 | 0 | 100 | 0 |

A variety of Brønsted and Lewis acids were also introduced to the reaction (Table 2). Many of these acids either failed to promote the reaction or caused decomposition of the material to mixtures of unidentifiable products (entries 1-5). When dimerization cleanly occurred, isoborreverine was almost exclusively produced (entries 6-9). The use of BF$_3$.Et$_2$ for an extended time led to the formation of only isoborreverine with complete conversion (entry 9). Methanolic HCl, however, provided the flinderoles as the major product (entry 10). Impressively, neat acetic acid produces only the flinderoles (entry 11). This selectivity is particularly notable given that neat TFA favors isoborreverine formation.

TABLE 2

1 Borrerine

Flinderole A 2
Desmethylflinderole C 4
Isoborreverine 7
Borreverine 6

| entry | acid (2 equiv) | solvent | temp | time | ratio of product yields[a,b] 2: | 4: | 7: | 6 |
|---|---|---|---|---|---|---|---|---|
| 1 | TfOH | benzene | 0-22° C. | 10 min | 0 | 0 | 0 | 0[c] |
| 2 | TfOH | benzene | 60° C. | 40 min | | decomp. | | |
| 3 | pTsOH | benzene | 0-22° C. | 60 min | 0 | 0 | 0 | 0[c] |
| 4 | TMSOTf | benzene | 60° C. | 40 min | 0 | 0 | 0 | 0[c] |
| 5 | AlCl$_3$ | benzene | 0-22° C. | 120 min | 0 | 0 | 0 | 0[c] |
| 6 | AlCl$_3$ | benzene | 60° C. | 40 min | 0 | 0 | 40 | 0[c] |
| 7 | Sc(Otf)$_3$ | benzene | 60° C. | 40 min | 0 | 0 | 38 | 0[c] |
| 8 | Tf$_2$O | benzene | 0° C. | 60 min | 0 | 0 | 50 | 0[c] |
| 9 | BF$_3$•OEt$_2$ | CH$_2$Cl$_2$ | 22° C. | 3 days | 0 | 0 | 100 | 0[c] |
| 10 | 1N HCl[d] | methanol | 55° C. | 2 h | 43 | 26 | 30 | 1[c] |
| 11 | CH$_3$COOH[e] | none | 55° C. | 18 h | 38 | 33 | 0 | 0[c] |

Three-Step Synthesis of Isoborreverine, Dimethylisoborreverine, Flinderoles A, B, C, and Des-Methylflinderole C The chemical structures of the natural organic compounds borrerine 1, flinderole A 2, flinderole B 3, des-methylflinderole C 4, flinderole C 5, borreverine 6, isoborreverine 7 and dimethylisoborreverine 8 are depicted in FIG. 1A. Although the synthetic methods described below can produce borreverine 6, it is not substantially formed, so these syntheses are directed to products shown to have anti-malarial activity.

Step 1: Preparation of Carbamates or Amides from Tryptamines:

Tryptamine 11 (1.28 g, 7.98 mmol) and 3-methyl 2-butenal (0.84 mL, 8.78 mmol) are dissolved in methylene chloride (40 mL) or another suitable non-acidic and non-nucleophilic organic solvent. 15 g of powdered 4 Å molecular sieves are added to the reaction mixture, and the reaction is stirred for 16 hrs or until complete at room temperature. Pyridine (2.48 mL, 31.9 mmol) or other base and methyl chloroformate (1.35 mL, 17.5 mmol) are added at 0° C., and stirring of the reaction is continued for 5 hrs at room temperature or until reaction is complete. The solution is filtered through celite or its equivalent to remove solids, which are washed with additional 40 mL of solvent. The organic layer is extracted with 1N HCl (2×30 mL), and this action is followed by washing with brine solution (20 mL). The solvent is dried over Na$_2$SO$_4$ or equivalent desiccant. Solvents are evaporated under vacuum. The solid residue is triturated with 10% ether in hexane (20 mL) or solvent mixtures of similar polarity. 1.97 g of a brown solid 12 is obtained (87% yield).

Step 2: Preparation of Borrerine 1 from Carbamate 12

The carbamate 12 (0.50 g, 1.67 mmol) or amide from Step 1 is dissolved in 25 mL of THF or similar aprotic solvent.

Figure 1B:
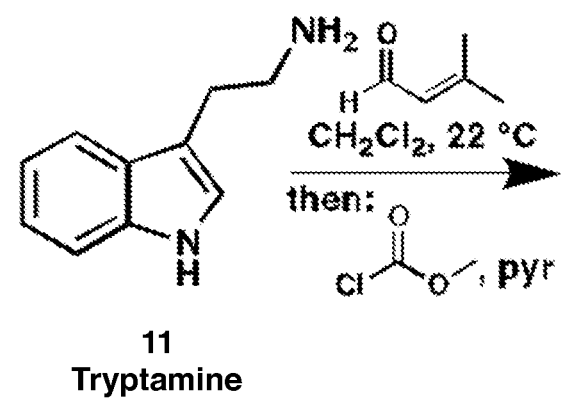
FIG. 1B is chemical synthetic scheme 1 depicting the synthesis of borrerine.
Figure 1B:
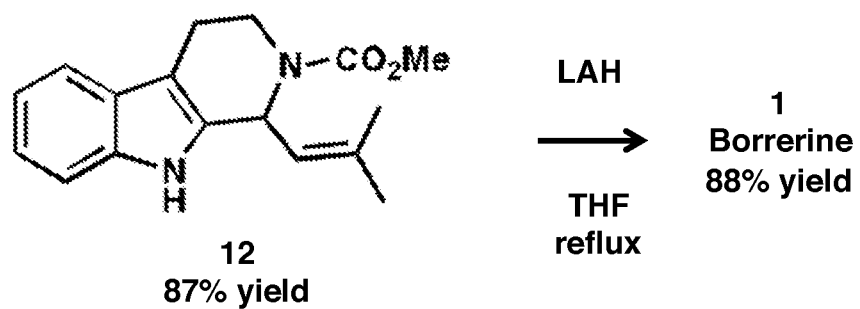

Lithium aluminum hydride (0.38 g, 10.06 mmol) is added at 0° C. in portions. Other strong reducing agents may also be used. The reaction mixture is stirred at reflux for 3 h or until reduction is complete, followed by quenching with 2 mL of water, 4 mL 1N NaOH, and 2 mL of water in sequence at −78° C. The resulting suspension is brought to room temperature and filtered, for example using a Buckner funnel. The solid obtained is washed with 10 mL of reaction solvent. The organic solvents are evaporated under vacuum. The water layer is extracted with methylene chloride (3×20 mL) or its equivalent. Methylene chloride is washed with brine (10 mL) and then dried over $Na_2SO_4$ or an equivalent desiccant. The crude material is purified using chromatography with approximately 96:4 dicloromethane:methanol or a similarly polar solvent as an eluent on silica gel. Borrerine is obtained as brownish yellow solid (88% yield). The synthesis of borrerine 1 is depicted in Scheme 2 (FIG. 1B).

Step 3A: Preparation of Flinderole A 2, Des-Methylflinderole C 4 and Isoborreverine 7 by Treatment of Borrerine 1 with Acid (Alternative A)

Figure 1C:
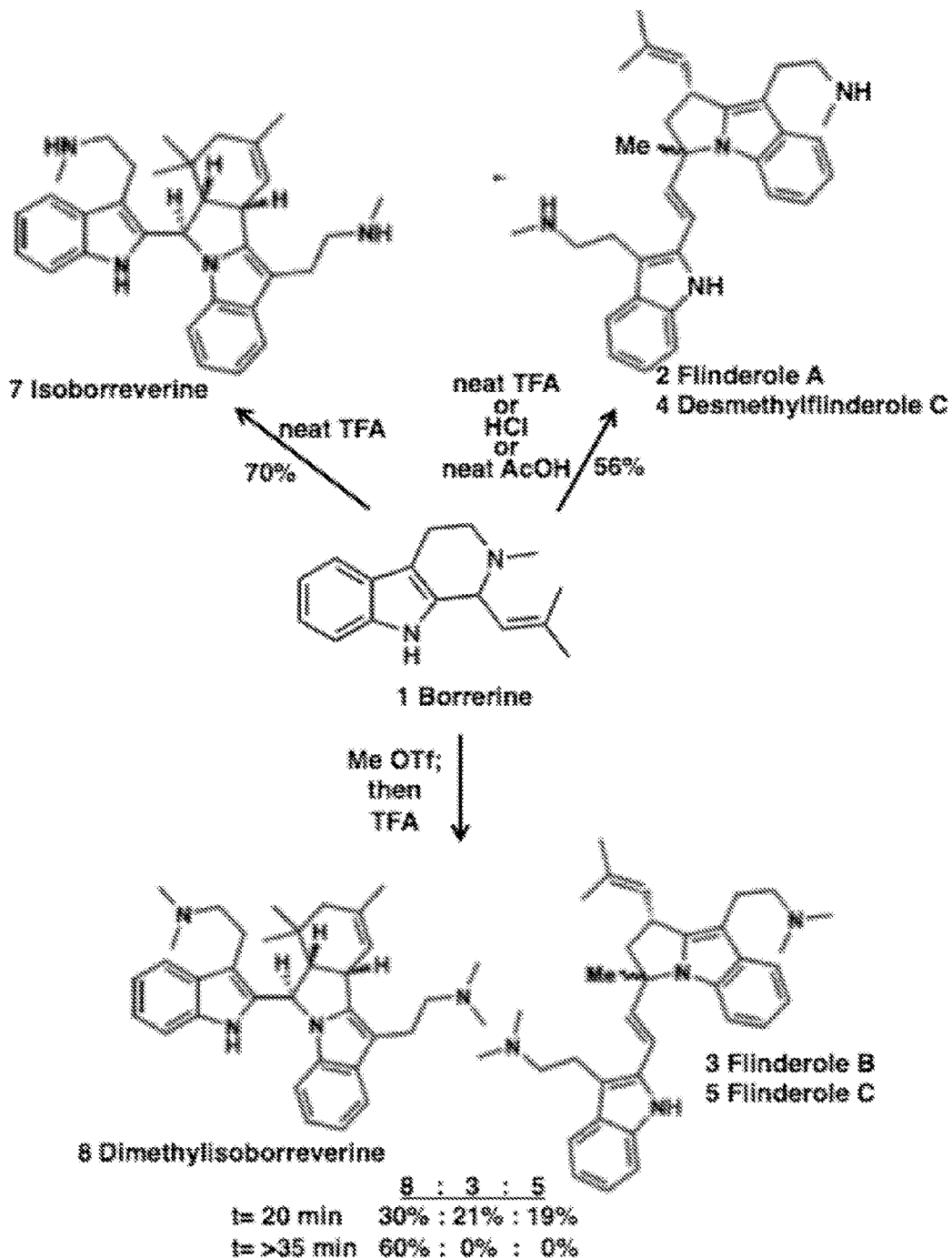
FIG. 1C is chemical synthetic scheme 2 showing the biomimetic synthesis of the *Flindersia* alkaloids as disclosed in the present invention.

The synthesis of flinderole A 2, des-methylflinderole C 4 and isoborreverine 7 is depicted in Scheme 3 (FIG. 1C). To 50 mg borrerine (0.208 mmol) from step (2), which is dissolved in 0.5 mL of an aromatic, alcoholic, halogenated, polar aprotic, or ethereal solvent, is added to trifluoroacetic acid (4.78 μL, 0.624 mmol) or other Brønsted acid, e.g., acetic acid, or Lewis acid, e.g., hydrochloric acid at room temperature. HCl in methanol is suitable for obtaining the flinderoles. The reaction is then stirred or heated (often to 45-65° C.) and stirred continually for 30 minutes. The solvents are evaporated under vacuum. Crude material is passed through silica gel using methanol or a similar polar solvent. Products are isolated using preparative HPLC.

Step 3B: Preparation of Flinderole B 3, Flinderole C 5 and Dimethylisoborreverine 8 by Treatment of Borrerine with Methyl Triflate Followed by Acid (Alternative B)

To 10 mg borrerine (0.041 mmol) from step (2), which is dissolved in 0.2 mL chloroform or similar non-nucleophilic solvent, is added MeOTf (4.56 μL, 0.041 mmol), dimethyl sulfate, or similar methylating reagent at 0° C. Trifluoroacetic acid or other Brønsted acid, e.g., acetic acid, or Lewis acid, e.g., hydrochloric acid, is added at 0° C., and the reaction mixture is then brought to room temperature and stirred for 30 minutes. The reaction is then quenched with 5 equivalents of amberlyst 21-A and stirred for 20 minutes at room temperature. The solution is filtered through cotton or similarly unreactive material, and the solvents are evaporated under vacuum. The crude material is purified using preparative HPLC.

Example 2

Figure 3:
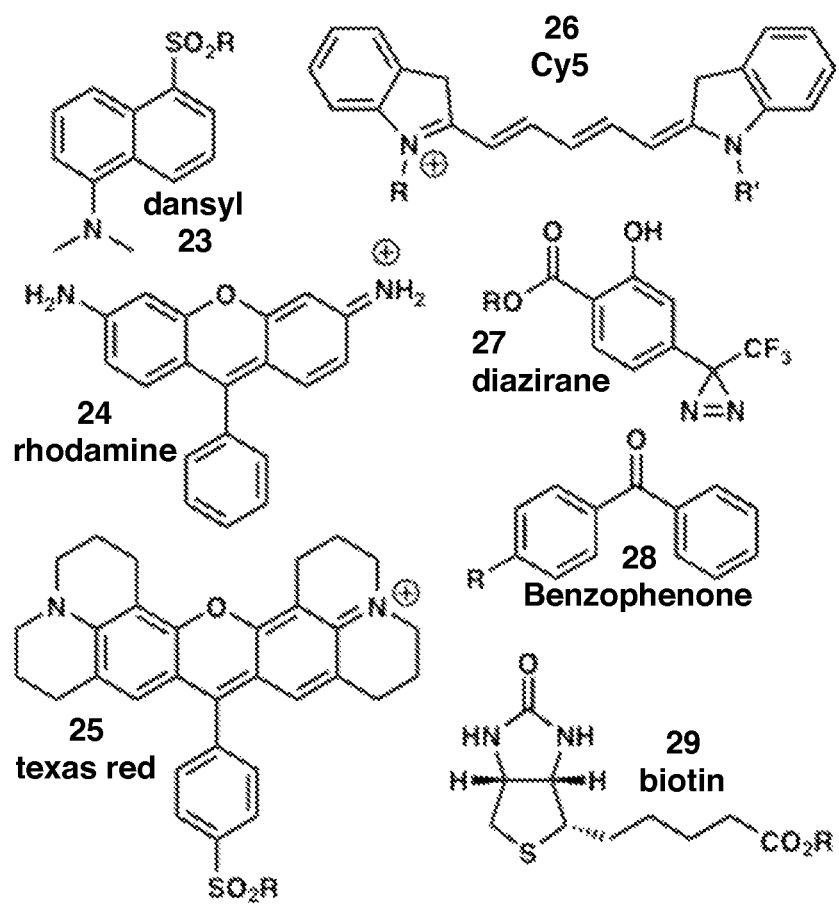
FIG. 3 is a nonexhaustive list of chemical groups useful for molecular biology.

Three-Step Synthesis of Analogs of Isoborreverine, Dimethylisoborreverine, Flinderoles A, B, C, and Des-Methylflinderole C General scheme for the synthesis of analog compounds is depicted in Schemes 3 and 4 (FIGS. 1D-1E) and may involve may involve one or more of the following steps. First there is access to heterodimers, i.e., two different borrerine derivatives reacting by incorporating an electron-donating group to stabilize imminium intermediate 20 and/or by adding an electron-withdrawing group to its reacting partner to destabilize a cationic imminium and increase the amount of diene 21 to ensure cross-reaction. Depending on the choice of conditions, this important extension will create a modified flinderole or isoborreverine, e.g., 22, with differentiated groups for further functionalization to 23. Secondly, combining this heterodimerization with a variety of aldehydes 14 and acid chlorides 15 will further increase library diversity. Thirdly, "Group 1" on compound 23 can be any element that forms a bond to oxygen that can be incorporated using standard techniques to one of ordinary skill in the art. Fourthly, "Group 2" is introduced using cross-coupling technology, benzyne chemistry, or metallation and reaction with an electrophile. Fifthly, groups, such as those in FIG. 3, may be incorporated, or additional functional groups such as heterocycles, pharmocophores, target recognition elements, cellular targeting groups, or cleavable groups can also be incorporated into borrerine for prodrug formulations. Compounds 23-26 are luminescent dyes, compounds 27 and 28 are alkylating and crosslinking groups, and biotin 29 allows the use of streptavidin for compound collection.

Derivative tryptamine compounds 13, derivate alkylating agents or aldehyde compounds 14 and derivative acylating group compounds 15 or other electrophilic N-addition compounds for derivative based synthesis (FIG. 2), as starting or intermediate materials are readily available for purchase or easily synthesized via routine synthesis in the art. Additional modifications are readily available via routine synthesis known and can also be used in the chemical synthetic schema.

Step 1: Preparation of Carbamates or Amides from Tryptamine Analogs or Derivatives 13

Possible derivatives of tryptamine, 3-methyl-2-butenal and methyl chloroformate are tryptamine derivative 13 and an α-,β-unsaturated aldehyde derivative 14 of 3-methyl 2-butenal are dissolved in methylene chloride or another suitable non-acidic and non-nucleophilic organic solvent. Powdered 4 Å molecular sieves or similar desiccant are added to the reaction mixture and stirred at room temperature. When imine formation is complete, pyridine and an acylating agent 15 are added at 0° C., and stirring is continued until the reaction is complete at room temperature. When the Pictet-Spengler reaction is finished, the solution is filtered through celite or its equivalent to remove solids, which are washed with additional solvent. The organic layer is extracted with aqueous acid followed by washing with brine solution. The solvent is dried over $Na_2SO_4$ or equivalent desiccant. Solvents are evaporated under vacuum. The solid residue is triturated with 10% ether in hexane (20 mL) or other solvent mixtures of appropriate polarity.

Step 2: Preparation of Borrerine Analogs and Derivatives

The carbamate or amide from step 1) is dissolved in THF or similar aprotic solvent. Lithium aluminum hydride is added at 0° C. in portions. Other strong reducing agents may also be used. The reaction mixture is stirred at reflux for until the reaction is complete, followed by quenching with water, 1N NaOH, and water in sequence at −78° C. The resulting suspension is brought to room temperature and filtered, for example using a Buckner funnel. The solid obtained is washed with reaction solvent. The organic solvents are combined and evaporated under vacuum. The water layer is extracted with methylene chloride or its equivalent. The methylene chloride is washed with brine and then dried over $Na_2SO_4$ or similar desiccant. The crude material is purified using chromatography.

Step 3A: Preparation of Flinderole A, Des-Me Flinderole C and Isoborreverine Analogs and Derivatives by Treatment of the Products of Step (2) with Acid (Alternative A)

To the borrerine derivative from step 2), which is dissolved an aromatic, alcoholic, halogenated, polar aprotic, or ethereal solvent, is added a Brønsted or Lewis acid, e.g., trifluoroacetic acid, acetic acid or hydrochloric acid, at room temperature. The reaction is then stirred or heated (often to 45-65° C.) and stirred continually until the starting material is consumed. The solvents are evaporated under vacuum. The crude material is passed through silica gel using methanol or a similar polar solvent. Products are isolated using preparative HPLC. Step 3B: Preparation of Flinderole B, C and Dimethylisoborreverine Analogs and Derivatives by Treatment of the Products of Step 2) with Methyl Triflate Followed by Acid (Alternative B)

To the borrerine derivative from step 2), which is dissolved in an aromatic, halogenated, polar aprotic, or ethereal solvent, is added MeOTf, dimethyl sulfate, or similar methylating reagent at 0° C. Trifluoroacetic acid or other Brønsted or Lewis acid, as described herein, is added at 0° C., and then the reaction mixture is brought to room temperature and stirred until the reaction is complete. The reaction is then quenched with 5 equivalents of amberlyst 21-A and stirred it for 20 minutes at room temperature. The solution is filtered through cotton or similarly unreactive material, and the solvents are evaporated under vacuum. The crude material is purified using preparative HPLC.

Figure 1D:
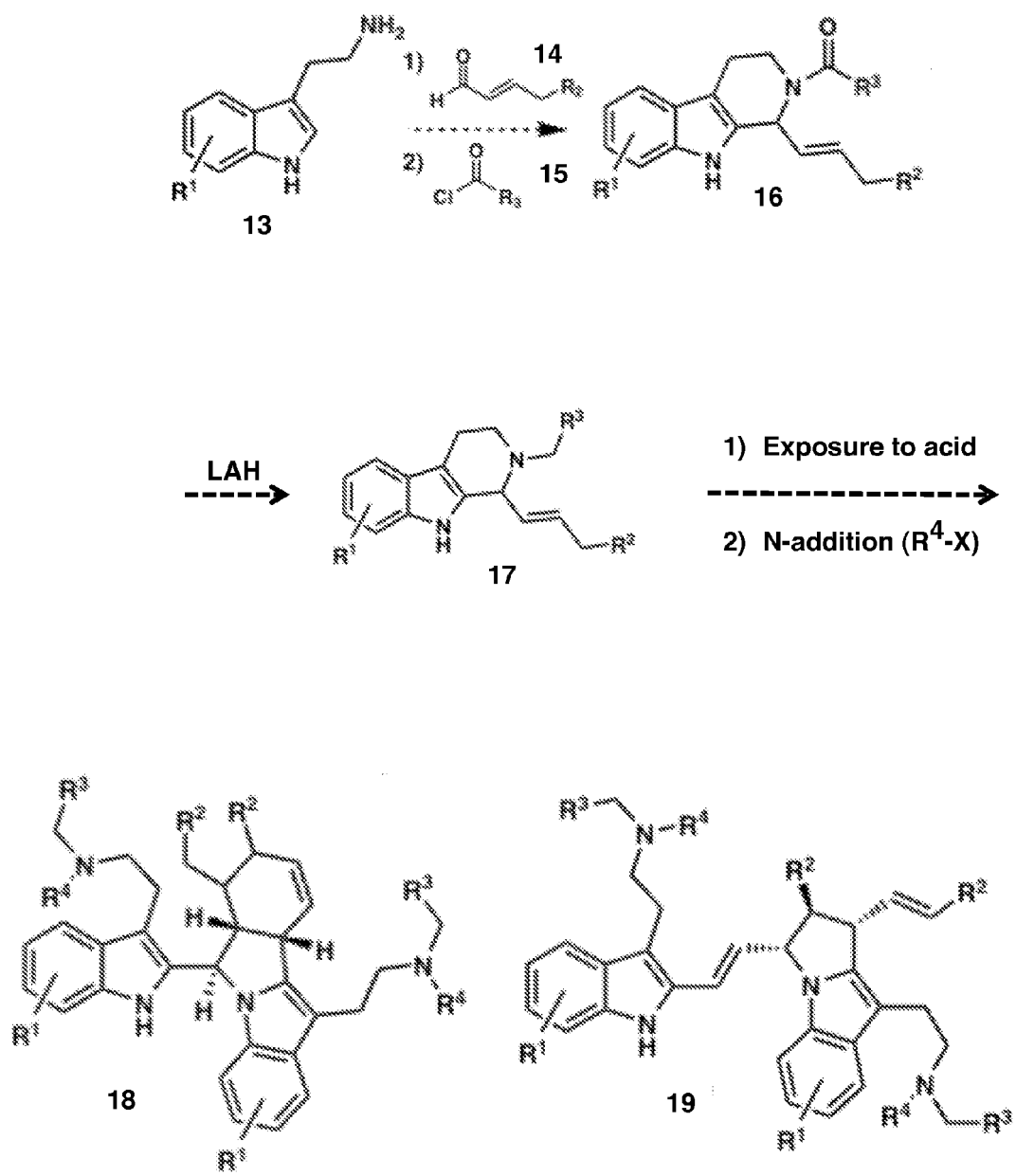
FIG. 1D is chemical synthetic scheme 3 showing the incorporation of chemical modifications of the tryptamine component 13, the enal component 14, and the acyl component 15 that highlights the position in 18 or 19 impacted by each of these modifications.
Figure 1E:
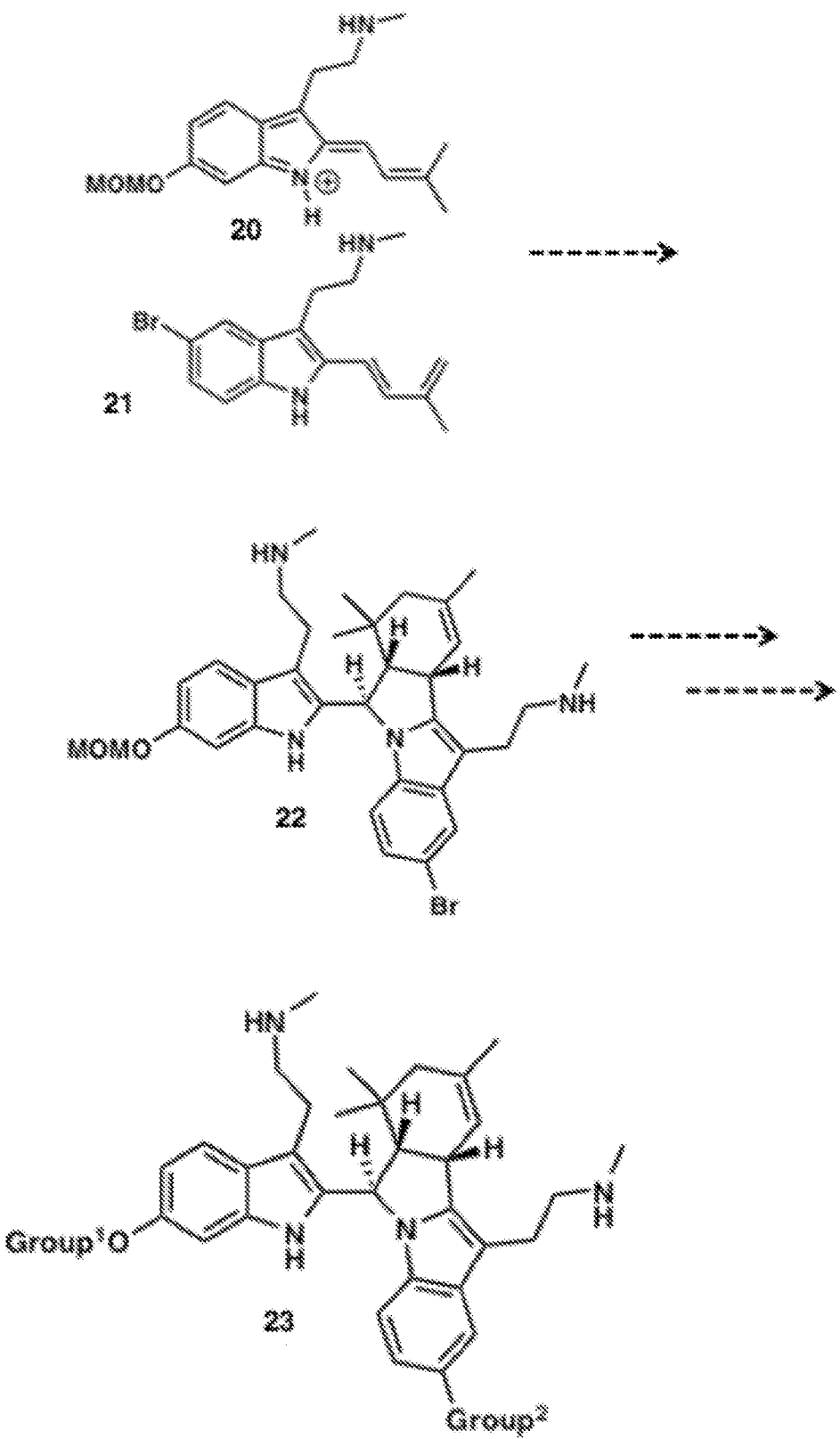
FIG. 1E is chemical synthetic scheme 4 showing the heterodimerization of Borrerine derivatives leads to alkaloid 22 and derivatives of 2 and 4. This approach, especially when used with a variety of aldehydes 14 and acid chlorides 15 (see FIG. 2), further increases library diversity. The inclusion of two different chemical functional groups is illustrated. Thus, additional functionalization can occur controllably at either or both of these two positions independently and in a controlled manner.

Specific examples of derivatives of tryptamine, the alkylating agent and the acylating agent that can be purchased or easily made are illustrated in FIG. 2. Many mono- and di-substituted tryptamines 13 are available. Electron donating and electron withdrawing groups around the aromatic ring can be used. Heteroatoms with free sites and halides are also useful as attachment points for additional diversity elements. The unsaturated aldehydes 14 also add a variety of functional groups while preserving the reactivity needed for the synthesis. The acylating and related alkylating agents 15 can be used for variation of the mono- or di-alkylated amines of compounds 18 and 19. Bisaldehydes, e.g., A, and bisacid chlorides, e.g., B, (FIG. 2) can be used to synthesize dimeric molecules or organize an intramolecular dimerization. Such a structure may be advantageous due to multi-valent reinforcement of activity. Specific derivative substituents of compounds 13, 14 and 15 appear in the final structures as $R^1$, $R^2$, $R^3$ and $R^4$, respectively, in Scheme 3 (FIG. 1D). Dimers and oligomers may form during the synthesis or post-synthesis as in Scheme 4 (FIG. 1E).

Example 3

Figure 4:
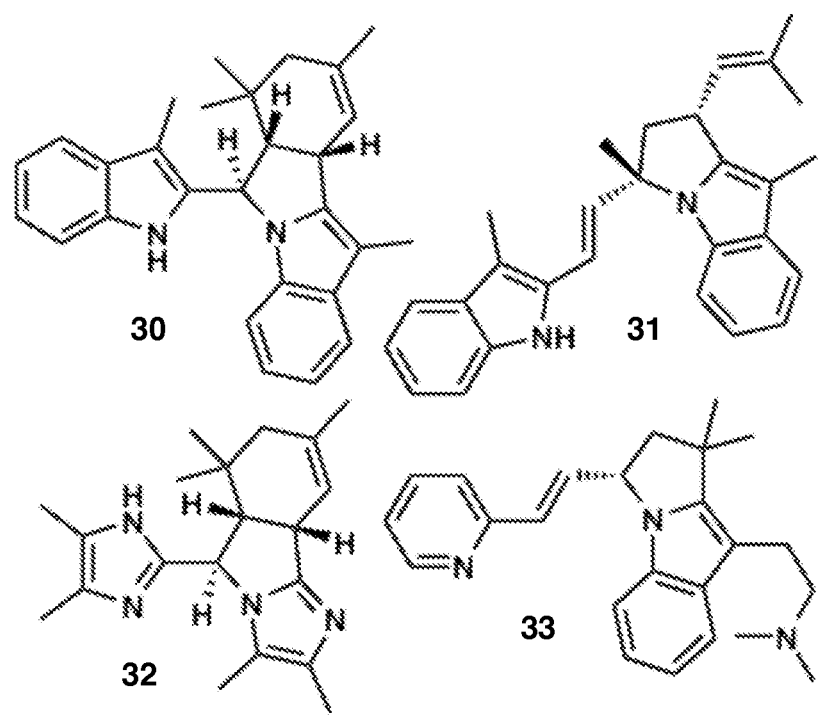
FIG. 4 is a nonexhaustive list of minimized derivative structures of *Flindersia* alkaloids produced by the synthetic methods described herein.

Determining Structure-Activity Relationships of the Borrerine Derivatives and Analogs Using the compound library produced from the use of modified compounds 13, 14, and 15 through the procedure described herein and the simplified structures in compounds 30-33 (FIG. 4) may be used to determine the atomic groups, i.e., pharmacophores, may be determined that are essential for the desired anti-malarial effects for the borreverine and flinderole carbon skeleton archetypes. If a small group of atoms is omitted in the synthesis and activity is lost, then those atoms must be linked to function. Nonessential structural elements can be omitted or simplified, as shown in FIG. 4, and compound properties, e.g., solubility, $pK_a$, etc., can be improved through the addition of atomic arrangements that confer beneficial traits, such as, heterocycles for additional hydrogen-bonding interactions, N-hydroxy amides, or bioisosteres of functional groups present, and/or through the removal of atomic structures that confer deleterious effects, such as but not limited to aromatic rings that are metabolically oxidized, redox active groups such as nitro groups and aldehydes, or chelating groups that sequester metal ions.

Other examples of functionality to add comprise, but are not limited to the purchase of a carboxylic acid-functionalized tryptamine derivative or inclusion of a carboxylic acid in a tryptamine derivative 13 through standard synthetic methods in order to increase the aqueous solubility of the alkaloid produced, which is desirable for bioavailability and other drug properties. In addition, fluorine atoms can be incorporated in the alkaloids by initial inclusion in 13, 14, and/or 15 either by purchasing the compounds or synthesis via standard techniques in order to mitigate metabolic degradation, the control of which is desirable for improving systemic drug half-life.

Also, the redox properties of the alkaloids can be adjusted using electron-donating and electron-withdrawing functional groups by their inclusion in 13, 14, and/or 15 either by purchasing the compounds or synthesis via standard techniques. Dimeric, oligomeric, or polymeric forms of the compounds can be synthesized using doubly functionalized bis-enals 14, bis-acylating agents 15, or bisfunctionalized linkers as "Group 1" or "Group 2" in Scheme 4 (FIG. 1E) and can be used to increase their efficacy by increasing their local concentration, or through interactions with multiple proteins simultaneously. In addition, extra aryl rings can be excluded from the parent structures following this method in order to reduce lipophilicity or intercalation problems to improve drug properties.

The following references are cited herein:
1. Fernandez et al. *Phytother Res* 2008, 22, 1409-1412.
2. Fernandez et al. *Org. Lett* 2009, 11, 329-332.
3. Fernandez et al. *Int. J. Antimicrob. Agents* 2010, 36, 275-279.
4. Yamanaka et al. *Heterocycles* 1984, 22, 371-374.
5. Dethe et al. *J Am Chem Soc* 2011, 133, 2864-2867.
6. Zeldin, R. M. and Toste, F. D. *Chem. Sci.* 2011, 2, 1706-1709.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:
1. A method for chemically synthesizing an analog of dimethylisoborreverine, comprising the steps of:
adding an alkylating agent to tryptamine derivatized independently at one or more of C4, C5, C6, and C7 with hydroxy, methoxy, acetoxy, benzyloxy, sulfomethyl, amino, acetate, methyl, ethyl, iso-propyl, t-butyl, trifluoromethyl, cyano, methylformate, nitrate, or halide;
adding an acylating agent in the presence of a base to form a substituted piperidinyl-N-carbamate intermediate;
adding a strong reducing agent to the intermediate to produce a borrerine derivative;
methylating the borrerine derivative with a methylating agent;
dimerizing the methylated borrerine derivative in the presence of trifluoroacetic acid to yield the dimethylisoborreverine analog.

2. The method of claim 1, wherein the alkylating agent is 3-methyl 2-butenal, the acylating agent is methyl chloroformate and the strong reducing agent is lithium aluminum hydride.

3. The method of claim 1, wherein the base is pyridine.

4. The method of claim 1, wherein the methylating agent is methyl triflate or dimethyl sulfate.

5. A chemical synthetic method for producing dimethylisoborreverine, comprising the steps of:
   synthesizing borrerine from tryptamine;
   methylating the synthesized borrerine; and,
   dimerizing the methylated intermediate in the presence of trifluroacetic acid to yield dimethylisoborreverine.

6. The method of claim 5, wherein the synthesizing step comprises:
   adding 3-methyl 2-butenal to tryptamine;
   adding methyl chloroformate in the presence of a base to form a substituted piperidinyl-N-carbamate intermediate; and
   adding a strong reducing agent to the intermediate to produce borrerine.

7. The method of claim 6, wherein the base is pyridine.

8. The method of claim 6, wherein the reducing agent is lithium aluminum hydride.

9. The method of claim 5, wherein the methylating agent is methyl triflate or dimethyl sulfate.

* * * * *